United States Patent [19]

McGarrigle

[11] Patent Number: 5,249,963
[45] Date of Patent: Oct. 5, 1993

[54] FLIP LID DISPENSER

[76] Inventor: Tamsen P. McGarrigle, 268 E. Main St., Moorestown, N.J. 08057

[21] Appl. No.: 826,410

[22] Filed: Jan. 27, 1992

[51] Int. Cl.$^5$ ............................................. A61C 3/00
[52] U.S. Cl. ................................ 433/163; 206/63.5; 224/217
[58] Field of Search .................. 433/49, 163, 229; 206/63.5, 815; 224/217, 218

[56] References Cited

U.S. PATENT DOCUMENTS

| | | | |
|---|---|---|---|
| 1,545,452 | 7/1925 | Pinn | 433/163 |
| 2,222,741 | 11/1940 | Bush | 224/217 |
| 2,356,722 | 8/1944 | Harris | 224/217 |
| 2,539,940 | 1/1951 | Abramson | 224/217 |
| 2,970,379 | 2/1961 | Hardgrove | 433/163 |
| 3,327,391 | 6/1967 | Malm | 433/163 |
| 4,844,308 | 7/1989 | Porteous | 224/217 |
| 4,901,847 | 2/1990 | Kesling | 206/63.5 |
| 4,991,759 | 2/1991 | Scharf | 224/217 |

*Primary Examiner*—John J. Wilson
*Attorney, Agent, or Firm*—Howson and Howson

[57] ABSTRACT

A finger-mounted thumb-actuated compact dispenser for use by a dental assistant to enable light curable compositions to be shielded from undesirable ambient light until such time as they are to be applied. The dispenser mounts on a finger and has a lid that can be opened and closed by a thumb. The dispenser minimizes interference with the user's hand and thereby frees both hands for assisting the dentist. This technique enables the dentist to perform the bonding procedure quickly and efficiently requiring less chair time.

3 Claims, 2 Drawing Sheets

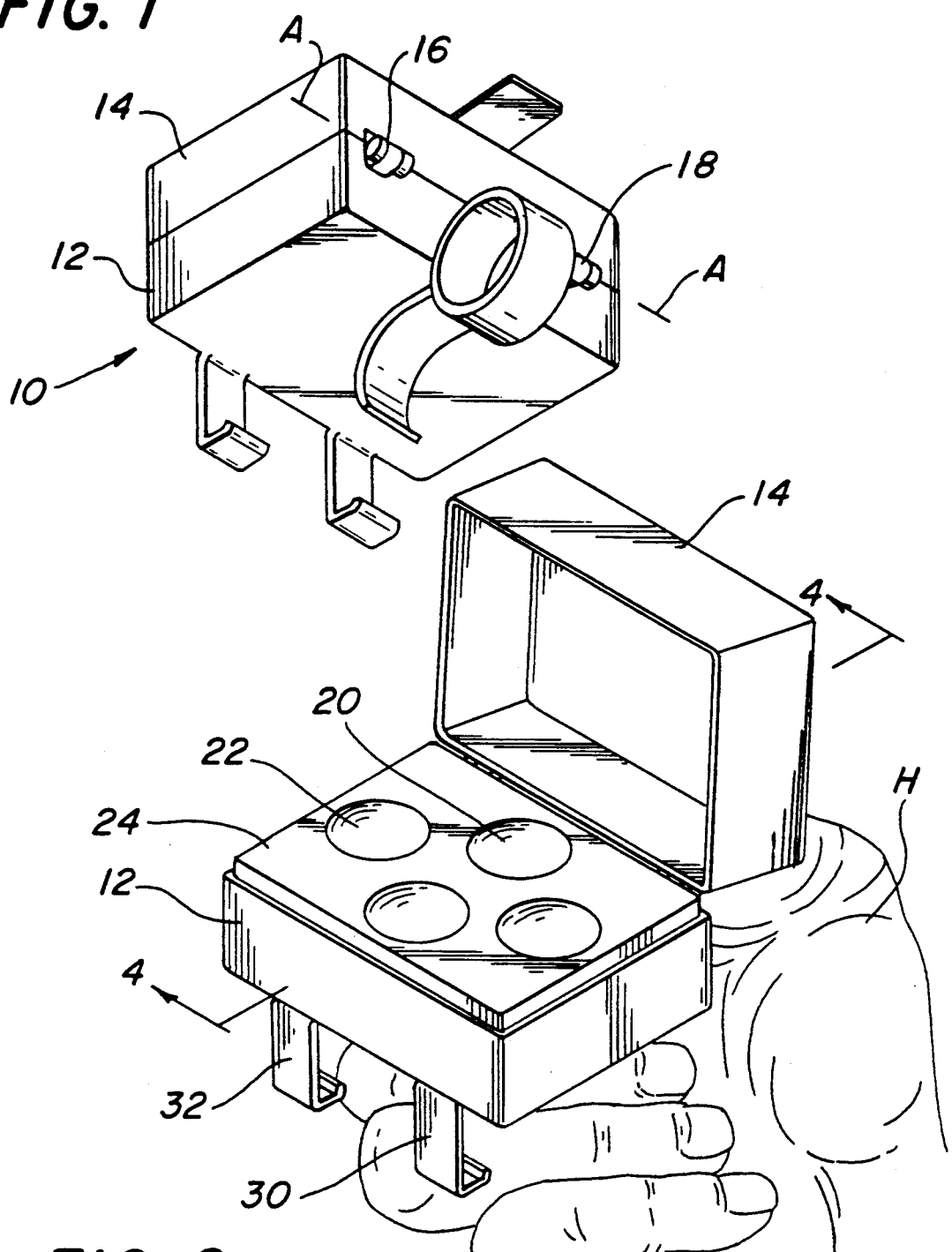

FLIP LID DISPENSER

FIELD OF THE INVENTION

The present invention relates to hand-held dispensers for dental materials, and more particularly, the present invention relates to a finger-mounted, thumb-actuated dispenser for light sensitive materials used in a dental operatory.

BACKGROUND OF THE INVENTION

In recent years, light curable substances have received wide-spread acceptance by dentists and patients. Such materials include resins and bonding agents which are applied to the teeth and cured in the presence of intense light. In order to prevent premature activation of the bonding agent, it is important that the material be shielded from excessive ambient light until such time as it is ready to be applied by the dentist. In a modern dental operatory, the dentist often works with a dental assistant. When working with light-curable compositions, the dental assistant customarily holds the container for the materials and opens and closes the material container lid as required to permit the dentist to access the material while minimizing its exposure to ambient light.

One proposed device for conveniently overcoming this problem is disclosed in U.S. Pat. No. 4,991,759 issued to Scharf. The Scharf patent discloses a clamshell-like container having a hinge permitting the lid to be opened and closed by means of the user's thumb while the container is supported from below by the user's fingers. While the Scharf container may provide certain advantages, it has certain limitations. For instance, the entire hand is occupied in holding and operating the container. This leaves the dental assistant with only the other hand to assist the dentist. A container which could be open and closed readily while enabling the dental assistant to have substantial use of both hands is highly desirable.

OBJECT OF THE INVENTION

With the foregoing in mind, a primary object of the present invention is to provide a novel device for conveniently containing and quickly dispensing light-curable materials in a dental operatory.

Another object of the present invention is to provide an improved hand-mounted dispenser for light-curable materials.

A further object of the present invention is to provide a unique small, compact dispenser which mounts and dismounts readily on the user's hand and affords substantial use of both hands in a dental operatory.

A still further object of the present invention is to provide a dental composition dispenser which is simple to use, thereby enabling dental procedures to be performed in less time.

SUMMARY OF THE INVENTION

More specifically, the present invention provides a finger-mounted container for use by a dental assistant to dispense light-curable materials in a convenient manner. The container includes a body portion adapted to contain light-curable materials and a normally-closed hinged lid portion. The body portion of the container has a ring enabling it to be mounted on a user's finger, and the lid has a handle enabling the user to open and close it with the thumb of the same hand. A stabilizer is provided adjacent the ring to stabilize the container in its dispensing position on the hand. The underside of the container body is provided with a pair of legs to support the container body substantially level while being filled with light-curable materials. The described device can be operated readily with two fingers of one hand, thereby freeing the palm and other fingers and enabling the dental assistant to have substantial use of both hands to assist the dentist.

BRIEF DESCRIPTION OF THE DRAWINGS

The foregoing and other objects, features and advantages of the present invention should become apparent from the following description, when taken in conjunction with the accompanying drawings in which:

FIG. 1 is a perspective view, from below, illustrating a dispenser embodying the present invention;

FIG. 2 is a perspective view of the dispenser of FIG. 1 shown mounted on a user's finger and in its open dispensing position;

DESCRIPTION OF THE PREFERRED EMBODIMENT

Figure 3:
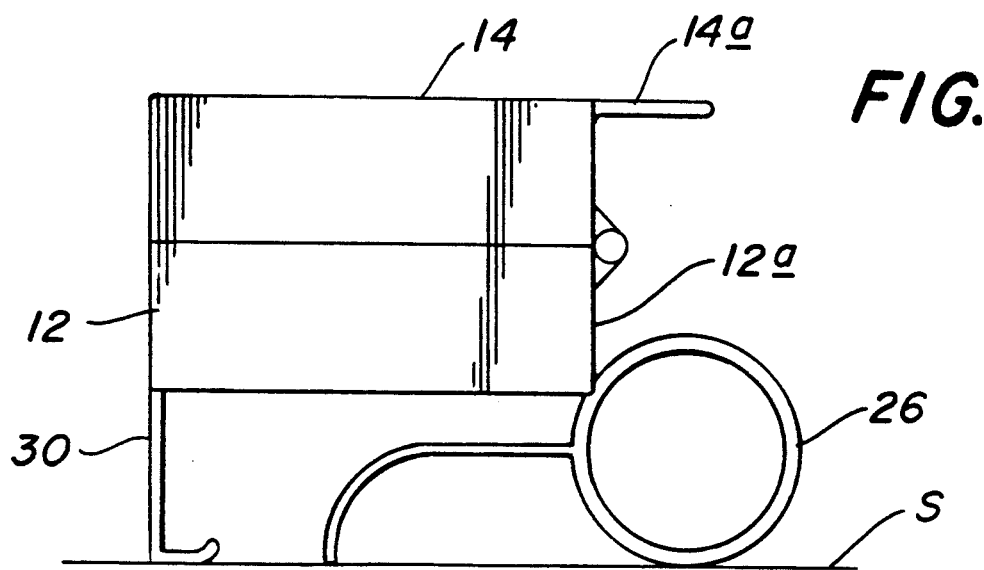
FIG. 3 is a side-elevational view of the dispenser.

Referring now to the drawings, FIG. 1 illustrates a flip lid dispenser 10 embodying the present invention. The dispenser 10 comprises a container having a body portion 12 and a lid portion 14 hinged to the body portion by a pair of hinges 16 and 18 which enable the lid 14 to pivot about an elongate axis extending along the rear of the container body 12. In FIG. 1, the dispenser 10 is illustrated in its closed position. In FIG. 2, the dispenser 10 is illustrated in its open position mounted on a user's hand H.

As best seen in FIG. 2, the inside of the container body 12 is divided into a series of shallowed depressions 20, 22 for receiving a light sensitive bonding material. Preferably, the depressions are formed in a block 24 of chemically inert material. Both the lid 14 and the container body 12 are preferably fabricated of light impervious plastic material so that when the lid 14 is closed on the container body 12, as illustrated in FIG. 1, the light-curable compositions contained in the cavities 20, 22 are shielded from ambient light. However, when the lid 14 is in its open position as illustrated in FIG. 2, access is provided to the material in the cavities 20 and 22.

Figure 4:
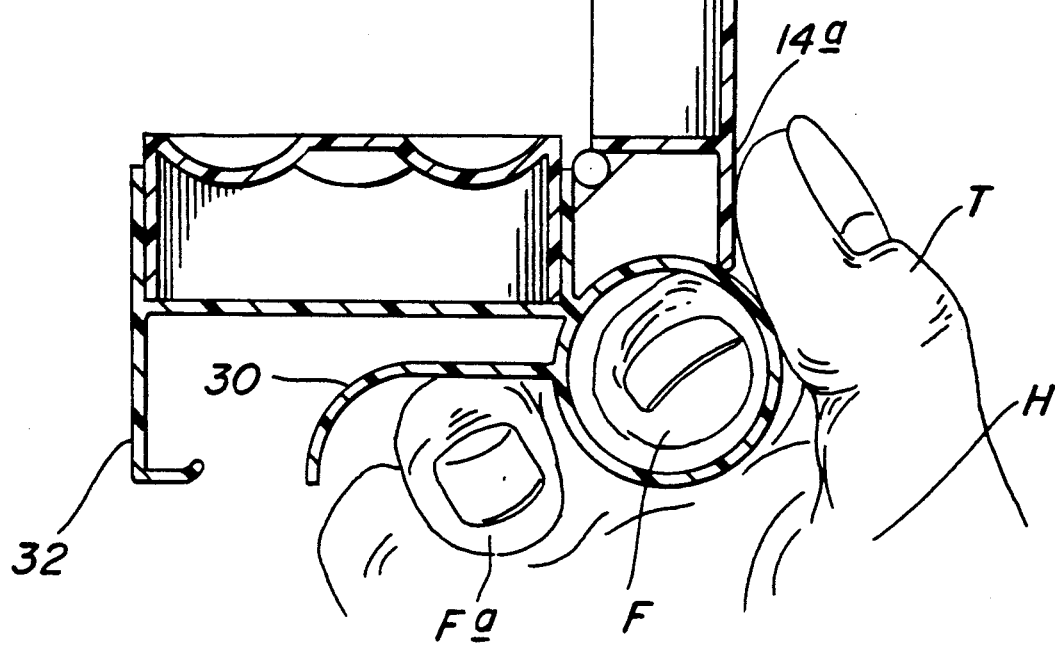
FIG. 4 is a sectional view taken on line 4—4 of FIG. 2.

In order to enable the dispenser 10 to be conveniently carried on the hand H of a health professional, such as a dental assistant, a ring 26 is provided at the rear end 12a of the container body 12 adjacent to the hinges 16 and 18. As illustrated in FIG. 1, the ring 26 is arranged in such a manner that it has an axis that extends substantially parallel to the hinge axis A of the lid 14 so that when the index finger of the user is inserted therein, such as illustrated in FIG. 4, the hinge axis A extends alongside and above the index finger. The lid 14 has a handle portion 14a which extends transversely of the hinge axis A and overlys the ring 26. Thus, when the index finger F of the user's hand H is inserted in ring 26, the user's thumb T can readily engage the handle 14a for pivoting the lid 14 about its access A into the open position illustrated in FIG. 2 affording access into the cavities 20 and 22. The handle length 14a may be adjusted relative to ring 26 to prevent it from opening too far and thereby enabling the lid 14 to pivot quickly by gravity about its axis A into the closed position illustrated in FIGS. 1 and 3, thereby minimizing exposure time to ambient light. This eliminates the need for a biasing spring to ensure closure.

For the purpose of preventing the dispenser 10 from rotating relative to the index finger F when mounted on the user's hand H, a stabilizer member 30 is provided for engaging one or more fingers adjacent to the index finger F. For instance, as illustrated in FIG. 4, the Finger $F_a$ adjacent to the index finger F may be disposed underneath the stabilizer member 30 in the manner shown to provide an anti-rotative action enabling the dispenser 10 to be maintained in a generally level position while mounted on the user's hand H. This is important because the light-curable bonding agents contained in the depressions 20 and 22 are in a fluid state and, therefore, capable of being spilled.

In order to maintain the dispenser 10 level while the bonding agents are being placed into the depressions 20 and 22, a pair of legs 30 and 32 are provided on the container body 12 in spaced relation with respect to the ring 26. Thus, when the dispenser 10 is placed on a support S such as illustrated in FIG. 3, the block 24 containing the cavities 20 and 22 is maintained substantially level enabling the liquid bonding agents to be placed into their respective cavities by the dental assistant.

In the illustrated embodiment, the ring 26, stabilizer member 30 and legs 32 are shown molded integral with the container body 12. It should be apparent, however, that these elements may be formed separately and attached to the container body, as by high strength adhesives. Molding, however, is preferred because of the manufacturing advantages realized.

From the foregoing, it should be apparent that the present invention provides an improved dispenser for light-curable compositions. The improved dispenser is advantageous because it is supported substantially on the upper portion of the user's hand in manner which enables the assistant to have substantially free use of the index finger and thumb when not actually holding the dispenser in its open position. As a result, the dental assistant can pass and receive the light curing wand and other instruments required by the dentist, thereby assisting the dentist quickly and efficiently through the procedure.

While a preferred embodiment of the present invention has been described in detail, various modifications, alterations and changes may be made without departing from the spirit and scope of the present invention as defined in the appended claims.

I claim:

1. A dispenser for containing and presenting a light-curable composition for delivery in a dental operatory, comprising:

a container having a receptacle portion for receiving a light-curable composition and having a lid portion hinged thereto for pivotal motion about an axis between open and closed positions;

ring means on said receptacle portion for receiving a user's finger and thereby mounting, said container thereto;

said ring means being located adjacent to and having an axis substantially parallel to said pivot axis of said lid, so that when the container is mounted on the finger, the lid axis extends lengthwise of and alongside said finger; and means providing on said lid a handle extending transverse to said lid pivot axis above said ring means for engagement by the user's thumb to open and close the lid;

whereby the other of the user's fingers are available for other functions while the container is mounted in its composition delivery position.

2. For use in containing a light-curable composition while preventing exposure to undesirable light until ready for delivery in a dental operatory, a compact hand-held dispenser, comprising:

a container body having a lid hinged for motion about an axis between a normally-closed containment position and an open delivery position;

ring means on said container body having an axis substantially parallel to the hinge axis, said ring means adapted to receive a user's finger to mount the container body thereon with the lid axis extending lengthwise of and alongside and above the finger;

handle means on said lid overlying the ring means and adapted to be engaged by the user's thumb when the container is in its delivery mode for opening the lid; and means carried beneath the container body for supporting the container in a level position on a support surface for enabling the composition to be placed therein for subsequent delivery;

whereby the container may be supported on the user's hand in a convenient manner.

3. A hand-held dispenser for user in a dental operatory to shield a light-curable composition from ambient light until such time as it is to be applied by a health professional, said dispenser comprising:

a container having a lid hinged about an axis to pivot between open and closed positions;

a ring on said container adjacent to said pivot axis for receiving a finger and enabling it to be disposed along the hinge lid pivot axis;

a handle on said container lid extending transverse to said lid pivot axis above said ring for engagement by a thumb when the ring is mounted on the finger;

means depending from the container in spaced relation with the ring for supporting the container in a level position for loading; and a stabilizer member located below said container and juxtaposed with respect to the ring to engage an adjacent finger when mounted on a user's hand for stabilizing the container in its delivery position when mounted on the user's hand;

whereby the composition in the container can be shielded from undesirable light by the closed lid and exposed for transfer to a work location by the health professional simply by pressing down on the lid handle with the thumb when the container is mounted on the user's fingers.

* * * * *